(12) United States Patent
Korth et al.

(10) Patent No.: US 7,951,796 B2
(45) Date of Patent: May 31, 2011

(54) 9-AMINO-ACRIDINE DERIVATIVES AND THEIR USE FOR ELIMINATING MISFOLDED PROTEINS

(76) Inventors: Carsten Korth, Düsseldorf (DE); Ralf Klingenstein, Hilden (DE); Stefan Löber, Rückersdorf (DE); Peter Gmeiner, Erlangen-Buckenhof (DE)

( * ) Notice: Subject to any disclaimer, the term of this patent is extended or adjusted under 35 U.S.C. 154(b) by 741 days.

(21) Appl. No.: 11/817,622

(22) PCT Filed: Feb. 28, 2006

(86) PCT No.: PCT/EP2006/060328
§ 371 (c)(1),
(2), (4) Date: Mar. 20, 2008

(87) PCT Pub. No.: WO2006/092395
PCT Pub. Date: Sep. 8, 2006

(65) Prior Publication Data
US 2009/0124001 A1    May 14, 2009

(30) Foreign Application Priority Data

Mar. 1, 2005    (DE) .......................... 10 2005 009 909

(51) Int. Cl.
| | |
|---|---|
| *A61K 31/55* | (2006.01) |
| *A61K 31/44* | (2006.01) |
| *A61K 31/497* | (2006.01) |
| *C07D 223/14* | (2006.01) |
| *C07D 223/18* | (2006.01) |
| *C07D 401/06* | (2006.01) |

(52) U.S. Cl. .................... 514/217; 514/297; 514/253.03; 540/586; 540/587; 544/361

(58) Field of Classification Search .................. 514/217, 514/297, 253.03; 544/361; 540/586, 587
See application file for complete search history.

(56) References Cited

U.S. PATENT DOCUMENTS

2004/0229898 A1   11/2004   Prusiner et al.

FOREIGN PATENT DOCUMENTS

| WO | 02/096431 | 12/2002 |
|---|---|---|
| WO | 03/059885 | 7/2003 |
| WO | 2004/032929 | 4/2004 |
| WO | 2004/092170 | 10/2004 |

OTHER PUBLICATIONS

May, Barnaby C.H. et al.; "Potent inhibition of scrapie prion replication in cultured cells by bis-aridines"; Proceedings of the National Academy of Sciences of USA, National Academy of Science, Washington, DC, US; vol. 100, No. 6; Mar. 18, 2003, pp. 3416-3421, XP002386930.

Kocisko, David A. et al.; "New inhibitors of Scrapie-Associated Prion Protein Formation in a Library of 2,000 Drugs and Natural Products"; Journal of Virology; The American Society for Microbiology, US; vol. 77, No. 19; Oct. 2003; pp. 10288-10294; XP008053706.

Korth, Carsten et al.; "Acridine and phenothiazine derivatives as pharmacotherapeutics for prion disease"; Proceedings of the National Academy of Sciences of USA; National Academy of Science, Washington, DC, US; vol. 98, No. 17; Aug. 14, 2001; pp. 9836-9841; XP002237386.

Prusiner, Stanley B. et al.; "Therapeutic Approaches to Prion Diseases"; Cold Spring Harbor Monograph Series; Cold Spring Harbor Laboratory; Cold Spring Harbor, NY, US; 2004; pp. 961-1014; XP009065375.

Bosque, Patrick J. et al.; "Cultured Cell Sublines Highly Susceptible to Prion Infection"; Journal of Virology; May 2000; pp. 4377-4386; vol. 74, No. 9.

Fischer, Marek et al.; "Prion protein (PrP) with amino-proximal deletions restoring susceptibility of PrP knockout mice to scrapie"; The EMBO Journal; vol. 15, No. 6; pp. 1255-1264; 1996.

Chandler, R.L, "Encephalopathy in Mice Produced by Inoculation With Scrapie Brain Material"; Lancet; Jun. 24, 1961; 1(7191): 1378-9.

*Primary Examiner* — James O Wilson
*Assistant Examiner* — Ebenezer Sackey
(74) *Attorney, Agent, or Firm* — Rankin, Hill & Clark LLP

(57) ABSTRACT

The invention relates to compounds according to general formula (1) and/or their enantiomers, diastereomers as well as their pharmaceutically compatible salts, and to the use thereof for producing a medicament suited for treating diseases associated with misfolded proteins.

25 Claims, 1 Drawing Sheet

9-AMINO-ACRIDINE DERIVATIVES AND THEIR USE FOR ELIMINATING MISFOLDED PROTEINS

Figure 1:
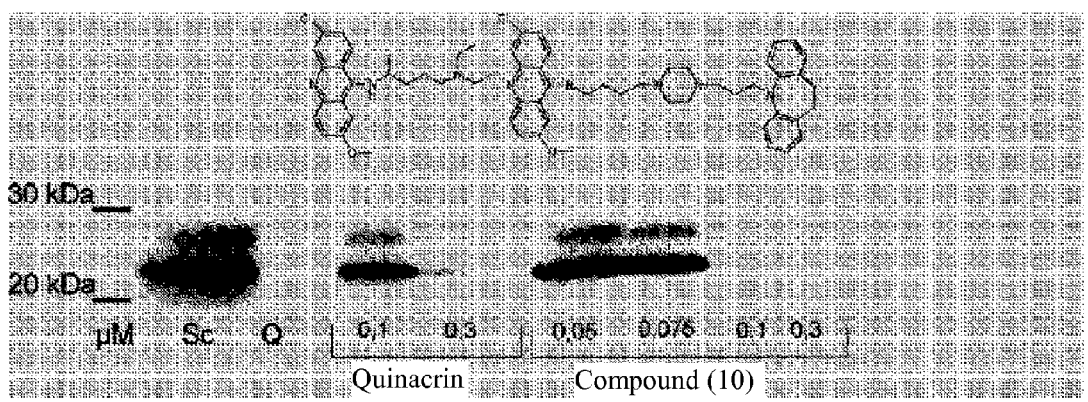

The invention relates to compounds, their enantiomers, diastereomers, and their pharmaceutically compatible salts, and their use to manufacture a medication as well as medications. The compounds are suited for treatment of diseases connected with misfolded proteins.

Prionic diseases are fatal neurodegenerative diseases that can appear both in humans, for example Creutzfeld-Jacob disease (CJD), and in the animal realm, for example bovine spongiform encephalopathy (BSE) in cattle, or scrapie in sheep. The infectious agent is so-called prion, which consists of a misfolded form of a protein that is present in the organism, the prion protein. In cases of disease, this prion accumulates in the central nervous system and there leads to cell death. Although these diseases rarely occur in humans, public focus has in recent years been directed to them, since it has been shown that BSE present in cattle can be transferred via the food chain to humans and can trigger CJD there.

Extracellular or intracellular protein aggregations are also a phenotypic sign of chronic degenerative diseases, especially neurodegenerative and/or neuropsychiatric diseases, for example Alzheimer's, Parkinson's or tauopathies.

In the state of the art, various substances are known that show effectiveness against prions. However, what is disadvantageous in the known substances is that due to their polarity, they cannot overcome the blood-brain barrier and thus cannot get into the brain. Moreover, many of the substances are not effective in low doses, but reveal a toxic effect at higher dosages.

The acridine and phenothiazine derivatives published in WO 02/096431, for example, reveal a disadvantage in that at low dosages, they are not effective or only slightly so. Additionally, acridine, especially bis-acridine, can have toxic effect. Also, these substances reveal merely a transient improvement in the disease symptoms, but no long-lasting therapeutic effect. This reveals a further disadvantage of the known substances, which manifest no effect in the stages of advanced or clinical disease.

The task of the present invention was to make available compounds that overcome at least one of the disadvantages of the state of the art. Particularly the task of the invention was to make compounds available that exhibit improved effectiveness against chronic degenerative diseases.

This problem is solved through compounds according to the overall formula (1) as indicated in what follows, and/or their enantiomers, diastereomers and their pharmaceutically compatible salts:

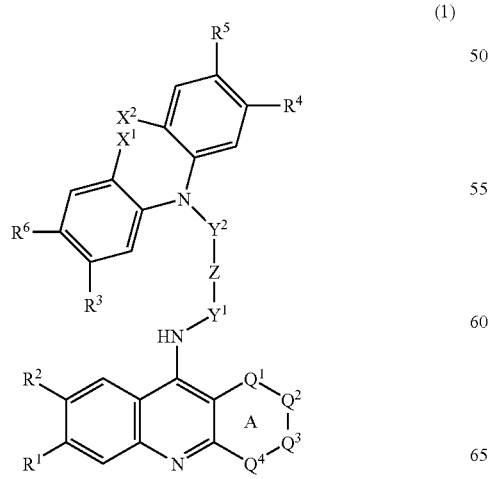

(1)

wherein:
A is a six-link, unsaturated or saturated ring;
$Q^1, Q^2, Q^3, Q^4$ are each selected, independent of each other, from the group including CH, C-halogen, C—O—($C_1$-$C_{10}$)-alkyl, C—$CF_3$, C—CN and/or $CH_2$;
$R^1, R^2, R^3, R^4, R^5, R^6$, are each selected, independent of each other, from the group including H, Halogen, $C_1$-$C_{10}$-alkyl, $C_1$-$C_{10}$-alkenyl, $C_1$-$C_{10}$-alkinyl, $C_1$-$C_{10}$-alkyloxy, $CF_3$, $NH_2$, $NHR^9$, whereby the radical $R^9$, is selected from the group including $C_1$-$C_{10}$-alkyl and/or $C_1$-$C_{10}$-acyl, $NO_2$, and/or CN;
$X^1, X^2$ each are H, or
$X^1$ and $X^2$ jointly form X, whereby:
X is selected from the group including $CH_2$, $CH_2$—$CH_2$, CH=CH, O and/or S;
$Y^1, Y^2$ each, independent from each other, are unbranched or branched $C_1$-$C_{10}$-alkyl;
Z is a structure element Z1 or Z2 as given above, whereby:
Z1 has the following general formula (2):

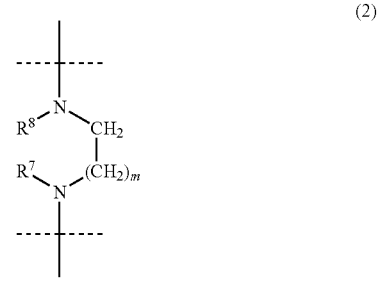

(2)

wherein:
m is 1, 2, 3, 4, 5 or 6,
$R^7, R^8$, are selected independently of each other from the group including H, $C_1$-$C_{10}$-alkyl, whereby $R^7$ and $R^8$, if necessary via a $CH_2$—$CH_2$ group, form a ring, and/or $C_1$-$C_{10}$-acyl;
Z2 has the following general formula (3):

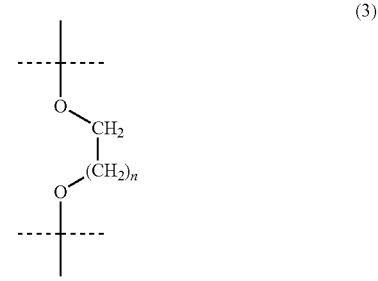

(3)

wherein
n is 2, 3, 4, 5 or 6.

Surprisingly, it was found that the invention-specific compounds can get through cell membranes.

A particular advantage of the compounds is hereby obtained, in that these compounds can be used in lower doses, which makes it possible to use the compounds particularly in humans.

Of particular advantage is that the invention-specific compounds exhibit reduced toxicity.

Surprisingly, it was further found that the invention-specific compounds can have a positive effect on misfolding of proteins.

Especially surprisingly, it was found that the secondary amino group in the side chain of the invention-specific compounds according to formula (1) can significantly increase the effectiveness compared to a tertiary amino group.

The structural element A is a six-link, unsaturated or partially saturated ring, whereby A is a carbon ring. $Q^1$, $Q^2$, $Q^3$, $Q^4$ include corresponding carbon atoms that form a carbon ring. The structural elements $Q^1$, $Q^2$, $Q^3$, and $Q^4$ can, in correspondence to the saturation of the A ring, form groups CH or $CH_2$.

The structural elements $Q^1$, $Q^2$, $Q^3$, and $Q^4$ can further have substituents on the carbon atoms, whereby the substituents are selected from the group that includes H, Halogen, $C_1$-$C_{10}$-alkyloxy, $CF_3$ and/or CN. Preferred substituents are selected, independent of each other, from the group including H, Halogen from the group including F, Cl and/or Br, and/or $C_1$-$C_5$ alkyloxy, preferably selected from the group including —O-methyl, —O-ethyl, —O-isopropyl and/or —O-tert-butyl.

The structural elements $Q^1$, $Q^2$, $Q^3$, and $Q^4$ can be appropriately selected independent of each other from the group including CH, $CH_2$ C-halogen, C—O—($C_1$-$C_{10}$)-alkyl, C—$CF_3$ and/or C—CN. Preferably the structural elements $Q^1$, $Q^2$, $Q^3$, and $Q^4$ are selected independent of each other from the group including CH, C-halogen and/or C—O—($C_1$-$C_{10}$)-alkyl, C—O-isopropyl and/or C—O-tert-butyl. Especially preferred are the structural elements $Q^1$, $Q^2$, $Q^3$, and $Q^4$ selected independent of each other from the group including Ch, C—Cl and/or C—O-methyl.

In preferred embodiment form, the structural element A is a six-link, unsaturated carbon ring. Additionally, the structural element $Q^2$ preferably has substituents. Preferably the structural elements $Q^1$, $Q^3$, and $Q^4$ each form a group CH and the structural element $Q^2$ is selected from the group including CH and/or C—O—$CH_3$.

In further preferred embodiment forms the structural element A is a six-link, partially saturated carbon ring, especially preferred a non substituted six-link, partially saturated ring. In these embodiment forms, preferably all the structural elements $Q^1$, $Q^2$, $Q^3$, and $Q^4$ form a $CH_2$ group.

The radicals $R^1$, $R^2$, $R^3$, $R^4$, $R^5$, and $R^6$ from the invention-specific compounds are each selected, independently of each other, from the group including H, Halogen, $C_1$-$C_{10}$-alkyl, $C_1$-$C_{10}$-alkenyl, $C_1$-$C_{10}$-alkinyl, $C_1$-$C_{10}$-alkyloxy, $CF_3$, $NH_2$, $NHR^9$, whereby the radical $R^9$, is selected from the group including $C_1$-$C_{10}$-alkyl and/or $C_1$-$C_{10}$-acyl, $NO_2$, and/or CN.

Preferably, the radicals $R^1$, $R^2$, $R^3$, $R^4$, $R^5$, and $R^6$ are each selected, independent of each other, from the group including H, halogen, selected from the group including F, Cl and/or Br, $NH_2$, $NHR^9$, whereby the radical $R^9$, is selected from the group including $C_1$-$C_{10}$-alkyl, preferably $C_1$-$C_5$-alkyl, preferably selected from the group including methyl, ethyl, isopropyl and/or tert-butyl, and/or $C_1$-$C_{10}$-acyl, preferably $C_1$-$C_5$-acyl, $NO_2$, $C_1$-$C_{10}$-alkyl, preferably selected from the group including methyl, ethyl, n-propyl, isopropyl, n-butyl, tert-butyl, n-pentyl, n-hexyl, n-heptyl and/or n-octyl, preferably $C_1$-$C_5$-alkyl, preferably selected from the group including methyl, ethyl, isopropyl and/or —O-tert-butyl. In preferred embodiment forms of the invention-specific compounds, the radicals $R^1$, $R^2$, $R^3$, $R^4$, $R^5$, and $R^6$ are each selected, independent of each other, from the group including H, Cl and/or —O-methyl, especially preferred, selected independent of each other from the group including H and/or Cl.

A substitution with groups $R^1$, $R^2$, $R^3$, $R^4$, $R^5$, and $R^6$ which are each selected independent of the other from the group including H and/or Cl, can result in a considerable increase in the effectiveness of the compound.

The structural elements $X^1$ and $X^2$ can each be H, or jointly form a structural element X. Embodiment forms including structural elements $X^1$ and $X^2$ each of which are H, can, for example, have a part structure according to the following formula (4):

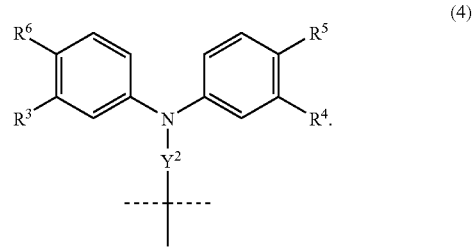

(4)

If structural elements $X^1$ and $X^2$ jointly form a structural element X, a part structure according to the following formula (5) is produced:

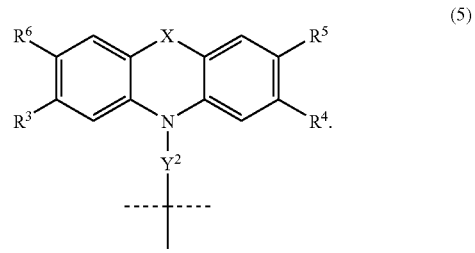

(5)

The structural element X can be a heteroatom, for example O or S, or be selected from the group including $CH_2$, $CH_2$—$CH_2$, and/or CH=CH. Preferably ring systems result, that have a central 6- or 7-link ring.

Especially preferred invention-specific compounds have a structural element X selected from the group including S and/or —$CH_2$—$CH_2$—.

Preferably the invention-specific compounds include a structural element Z1. Preferred embodiment forms including a structural element Z1 have the following formula (6):

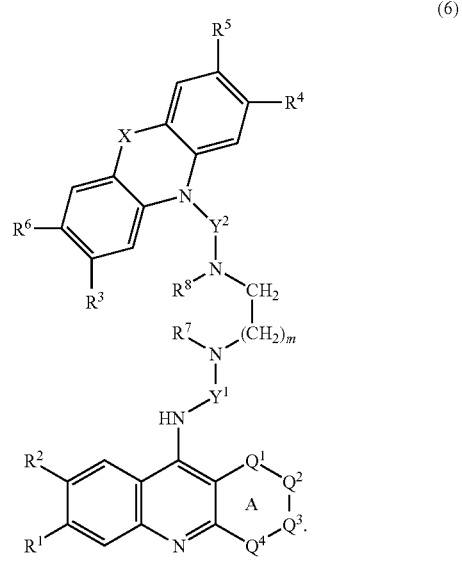

(6)

The radicals $R^7$ and $R^8$ are preferably H or alkyl groups with $C_1$ to $C_{10}$ like methyl, ethyl, n-propyl, isopropyl, n-butyl, tert-butyl, n-pentyl, n-hexyl, n-heptyl and/or n-octyl, preferably $C_1$-$C_5$-alkyl, especially selected from the group including methyl, ethyl, isopropyl and/or tert-butyl. In these embodiment forms, m preferably is 1, 2, 3, 4, 5 or 6.

Preferably the structural element Z1 has a ring-shaped structure, whereby the ring closes via the radicals $R^7$ and $R^8$. Preferably the ring is formed by each of the radicals $R^7$ and $R^8$ forming a $CH_2$ group, and jointly forming a $CH_2$—$CH_2$ group. In these embodiment forms, m is preferably 1 or 2, so that a heterocyclic 6- or 7-link ring is formed.

In preferred embodiment forms, m is equal to 1 and the structural element Z1 includes a piperazine heterocycle. The structural element Z1 correspondingly has the following formula (7) in preferred embodiment forms:

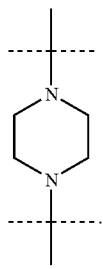

(7)

Additional preferred embodiment forms including a structural element Z2 have the following formula (8), whereby n preferably is 2, 3, 4 or 5:

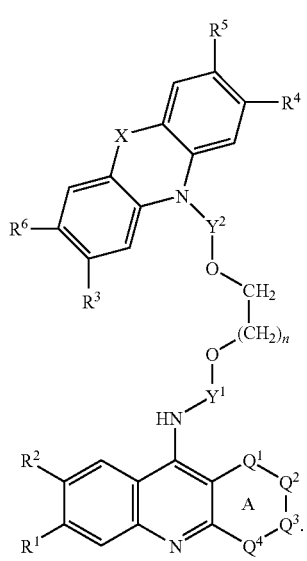

(8)

The structural elements $Y^1$, $Y^2$ are each, independent from each other, an unbranched or branched $C_1$-$C_{10}$-alkyl.

Especially preferred compounds and/or their enantiomers, diastereomers as well as their pharmaceutically compatible salts, have the overall formula (9), as given next:

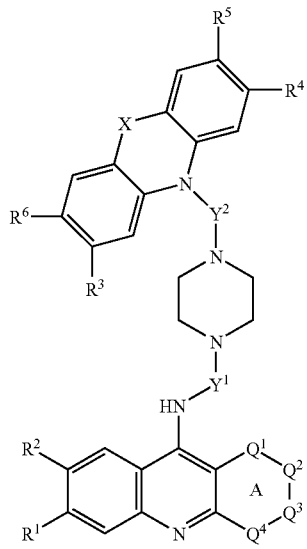

(9)

wherein:
A is a six-link, unsaturated or saturated ring;
$Q^1$, $Q^2$, $Q^3$, $Q^4$ are each selected, independent of each other, from the group including CH, C-halogen, C—O—($C_1$-$C_{10}$)-alkyl, C—$CF_3$, C—CN and/or $CH_2$;
$R^1$, $R^2$, $R^3$, $R^4$, $R^5$, $R^6$, are each selected, independent of each other, from the group including H, Halogen, $C_1$-$C_{10}$-alkyl, $C_1$-$C_{10}$-alkenyl, $C_1$-$C_{10}$-alkinyl, $C_1$-$C_{10}$-alkyloxy, $CF_3$, $NH_2$, $NHR^9$, whereby the radical $R^9$, is selected from the group including $C_1$-$C_{10}$-alkyl and/or $C_1$-$C_{10}$-acyl, $NO_2$, and/or CN;
X is selected from the group including $CH_2$, $CH_2$—$CH_2$, CH=CH, O and/or S;
$Y^1$, $Y^2$ each, independent from each other, are unbranched or branched $C_1$-$C_{10}$ alkyl.

Preferably the structural elements $Q^1$, $Q^2$, $Q^3$, and $Q^4$ of the invention-specific compounds each form a CH group and the structural element $Q^2$ is selected from the group including CH and/or C—O—$CH_3$. In especially preferred embodiment forms, the structural elements $Q^1$, $Q^3$, and $Q^4$ each form a $CH_2$ group, and the structural element $Q^2$ is C—O—$CH_3$. In further preferred embodiment forms, preferably all the structural elements $Q^1$, $Q^2$, $Q^3$, and $Q^4$ form a $CH_2$ group.

Preferably, the radicals $R^1$, $R^2$, $R^3$, $R^4$, $R^5$, and $R^6$ are each selected, independent of each other, from the group including H, halogen, selected from the group including F, Cl and/or Br, $NH_2$, $NHR^9$, whereby the radical $R^9$, is preferably selected from the group including $C_1$-$C_5$-alkyl, preferably selected from the group including methyl, ethyl, isopropyl and/or tert-butyl, and/or $C_1$-$C_{10}$-acyl, preferably $C_1$-$C_5$-acyl, $NO_2$, $C_1$-$C_5$-alkyl, preferably selected from the group including methyl, ethyl, isopropyl, and/or tert-butyl, and/or $C_1$-$C_5$-alkyloxy, preferably selected from the group including —O-methyl, —O-ethyl, —O-isopropyl and/or —O-tert-butyl. In preferred embodiment forms of the invention-specific compounds, the radicals $R^1$, $R^2$, $R^3$, $R^4$, $R^5$, and $R^6$ are each selected, independent of each other, from the group including H, Cl and/or —O-methyl, especially preferred, selected independent of each other from the group including H and/or Cl.

Especially preferred compounds have a structural element X selected from the group including S and/or $CH_2$—$CH_2$.

The structural elements $Y^1$ and $Y^2$ of the invention-specific compounds can each, independent of the other, have at least one branching, whereby methyl and/or ethyl side chains are preferred. Preferably, the structural elements $Y^1$ and $Y^2$ are each selected, independent of each other, from the group including —(CH$_2$)$_o$—, whereby o is 2, 3, 4, 5 or 6, preferably 3 or 4, and/or —CH(CH$_3$)—(CH$_2$)$_p$—, whereby p is 2, 3, 4, or 6, preferably 3 or 5, especially preferred 3. In very particularly preferred embodiment forms, the structural elements Y$^1$ and Y$^2$ are each, independent of each other, —(CH$_2$)$_o$—, whereby o is 3, 4 or 5.

In especially preferred compounds, the distance formed by the group of structural elements Y$^1$—Z—Y$^2$ between each of the nitrogen atoms connecting to the structural elements Y$^1$ and Y$^2$ is a length from 10 Å to 15 Å.

Especially preferred compounds have the structural elements Q$^1$, Q$^3$, and Q$^4$ each of which forms a CH$_2$ group, and a structural element Q$^2$ selected from the group including CH and/or C—O—CH$_3$. whereby the structural element Q$^2$ preferably is C—O—CH$_3$, and structural elements Y$^1$ and Y$^2$ which, independent of each other, are each selected from the group including —(CH$_2$)$_o$— and/or —CH(CH$_3$)—(CH$_2$)$_p$—, whereby o is 2, 3, 4, 5 or 6, and p is 2, 3, 4 or 5.

Additional preferred compounds have the structural elements Q$^1$, Q$^3$, and Q$^4$ each of which forms a CH$_2$ group, and a structural element Q$^2$ selected from the group including CH and/or C—O—CH$_3$. whereby the structural element Q$^2$ preferably is C—O—CH$_3$, and structural elements Y$^1$ and Y$^2$ which, independent of each other, are —(CH$_2$)$_o$—, whereby o is 3, 4, or 5.

Very particularly suitable compounds include structural elements Q$^1$, Q$^3$, and Q$^4$ each of which forms a CH$_2$ group, and a structural element Q$^2$ selected from the group including CH and/or C—O—CH$_3$. whereby the structural element Q$^2$ preferably is C—O—CH$_3$, and structural elements Y$^1$ and Y$^2$ which, independent of each other, are —(CH$_2$)$_o$—, whereby o is 3, 4, or 5, and the radicals R$^1$, R$^2$, R$^3$, R$^4$, R$^5$ and R$^6$, each selected, independent of the other, from the group including H and/or Cl.

Especially preferred embodiment forms of the invention-specific compounds have the formula (10) given as follows, and/or are their enantiomers, diastereomers as well as their pharmaceutically compatible salts:

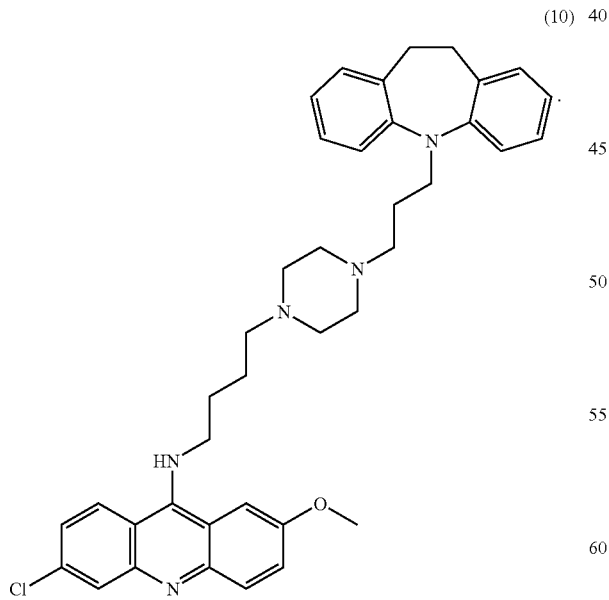
(10)

Further preferred embodiment forms of the invention-specific compounds have the formula (11) given next, and/or are their enantiomers, diastereomers as well as their pharmaceutically compatible salts:

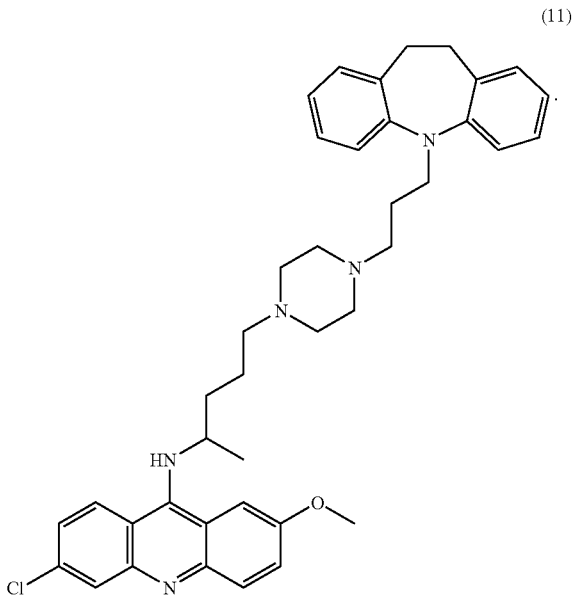
(11)

Also preferred embodiment forms of the invention-specific compounds have the formula (12) given next, and/or are their enantiomers, diastereomers as well as their pharmaceutically compatible salts:

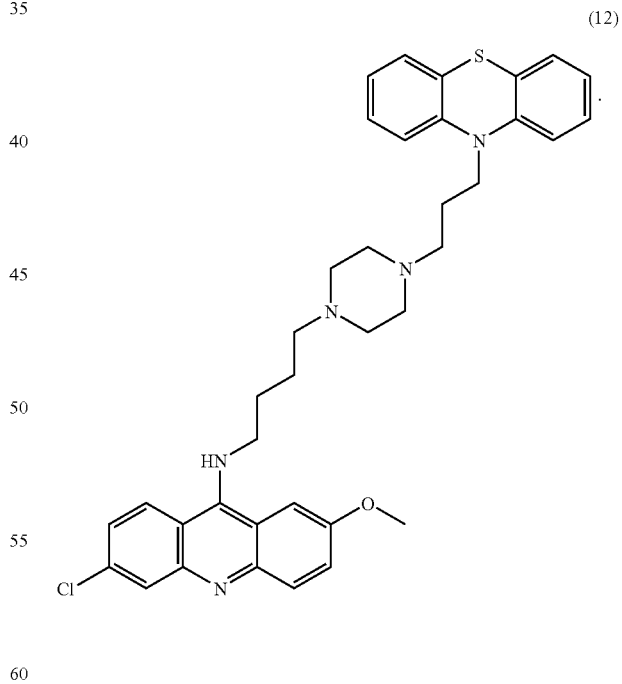
(12)

Also preferred embodiment forms of the invention-specific compounds have the formula (13) given next, and/or are their enantiomers, diastereomers as well as their pharmaceutically compatible salts:

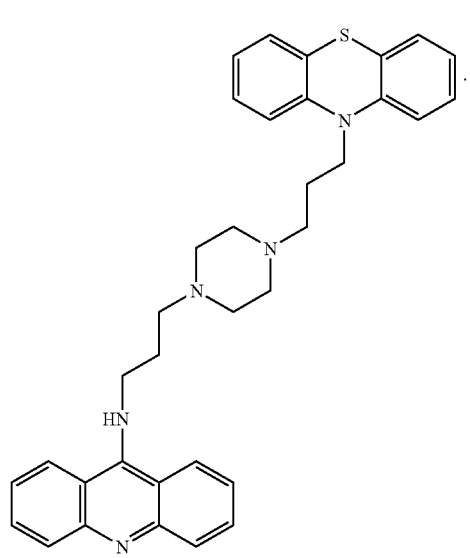
(13)

Also preferred embodiment forms of the invention-specific compounds have the formula (14) given next, and/or are their enantiomers, diastereomers as well as their pharmaceutically compatible salts:

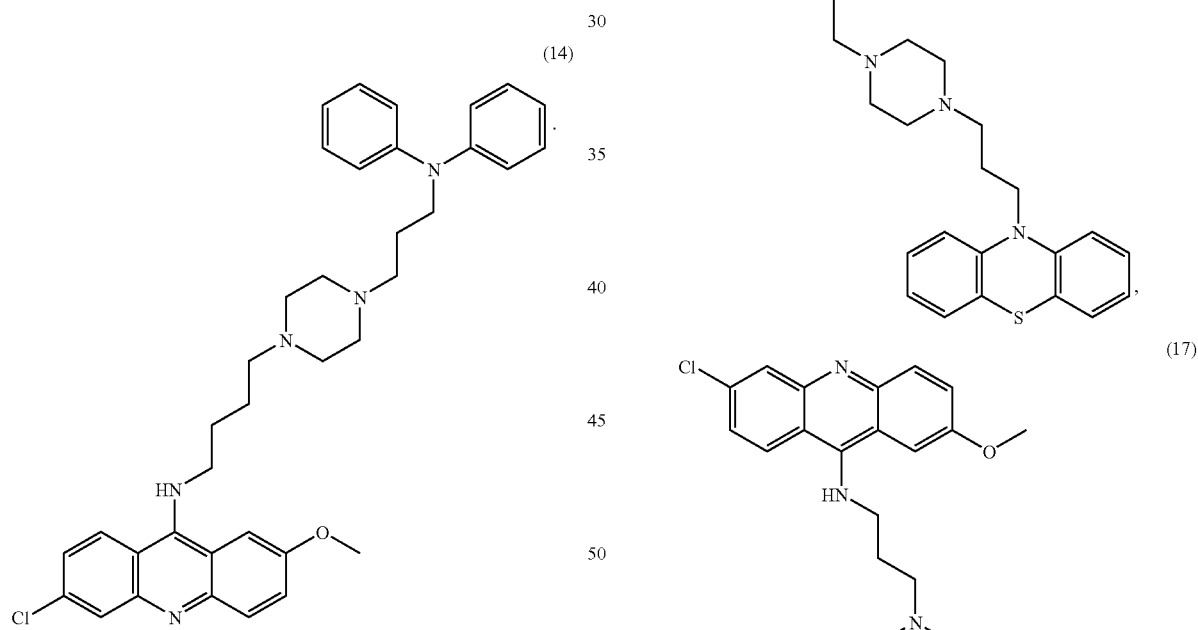
(14)

Preferred compounds are selected from the group including (6-chlor-2-methoxy-acridine-9-yl)-(4-{4-[3-(10,11-di-hydro-dibenzo[b,f]azepine-5-yl)-propyl]-piperazine-1-yl}-butyl)-amine and/or (6-chlor-2-methoxy-acridine-9-yl)-(3-{4-[3-(dihydro-dibenzo[b,f]azepine-5-yl)-propyl]-piperazine-1-yl}-butyl)-amine, whereby the first-name corresponds to compound (10).

Further preferred embodiment forms of the invention-specific compounds have the formulas (15) to (24) given next, and/or are their enantiomers, diastereomers as well as their pharmaceutically compatible salts:

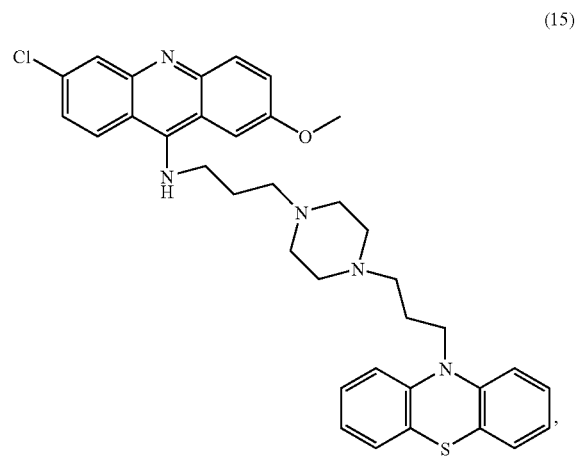
(15)

(16)

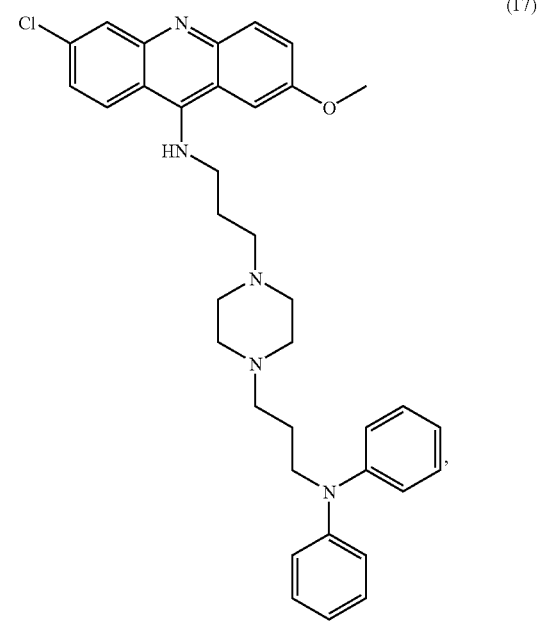
(17)

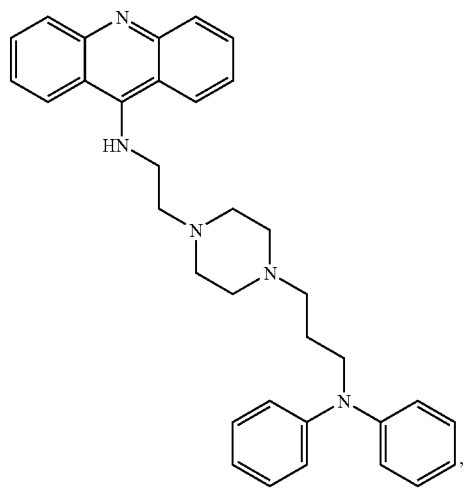
(18)
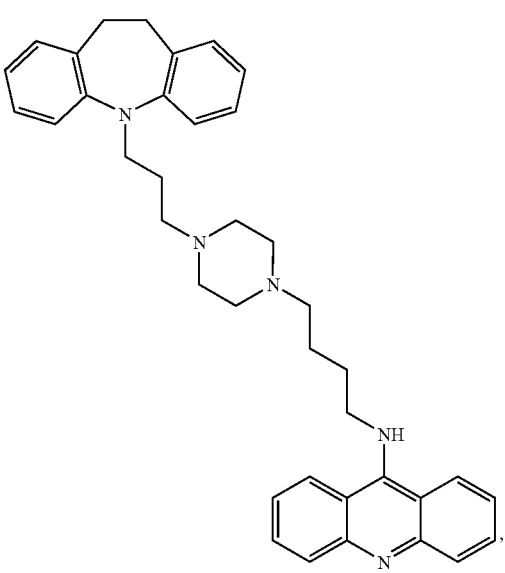
(19)
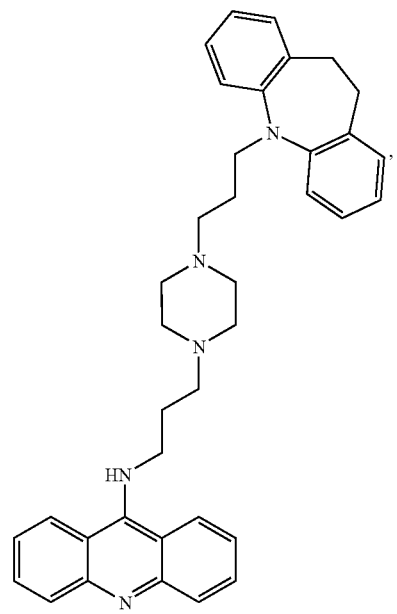
(20)
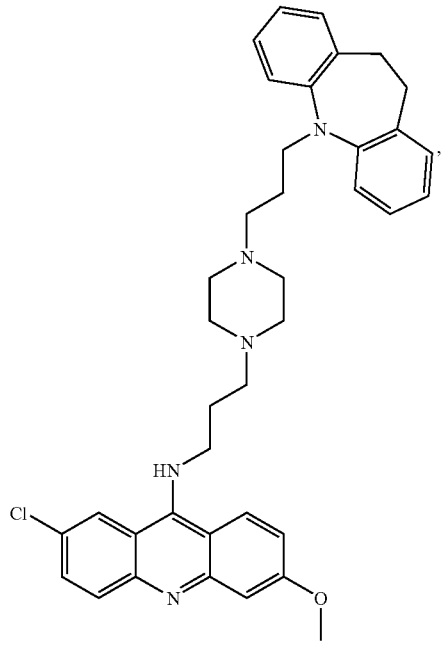
(21)
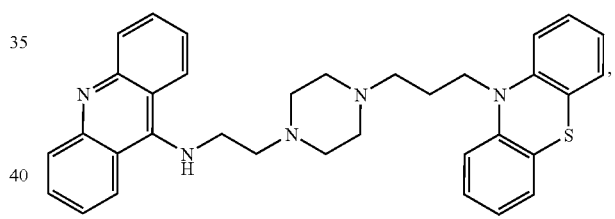
(22)
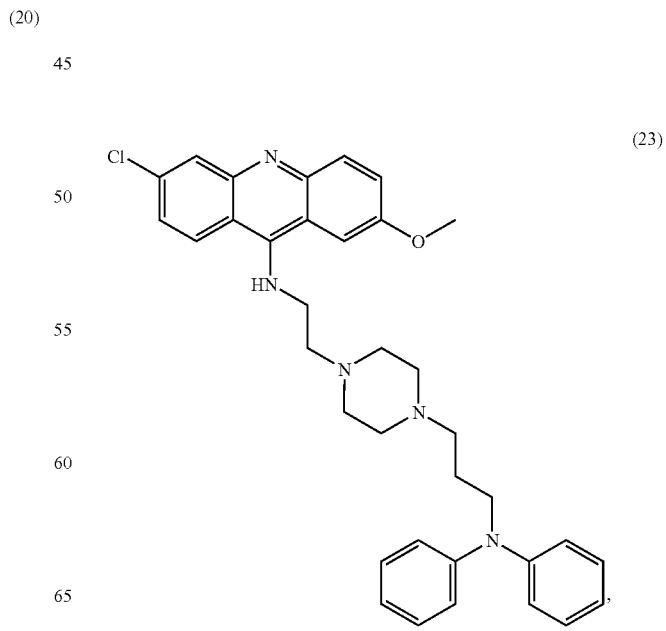
(23)

-continued (24)

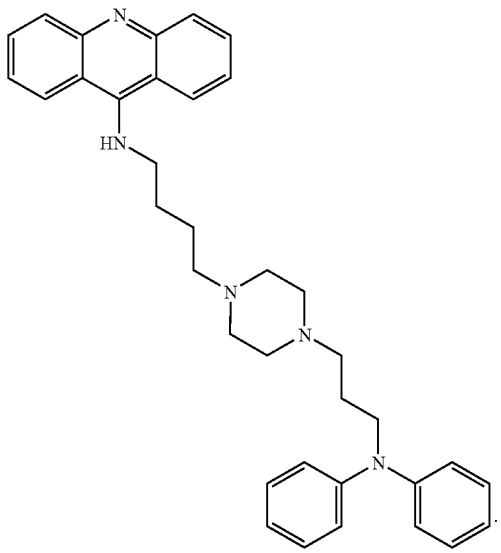

The compounds can be manufactured according to the customary synthesis methods.

One advantage of the compounds lies in preferred embodiment forms in that these compounds can get through cell membranes. In particular, the invention-specific compounds have good ability to pass the blood-brain barrier. This makes it possible for the invention-specific compounds to be used in vivo and in vitro. Invention-specific compounds can be used, for example, in cell cultures. In especially preferred embodiment forms, invention-specific compounds are also usable in tissues or organs. Particularly, the invention-specific compounds make it possible to use them in organisms.

Due to their advantageous properties, the invention-specific compounds are suitable for use as medications.

A further subject of the invention is the use of the invention-specific compounds, particularly compounds with the overall formulas (10) to (14), to produce a medication.

The invention-specific compounds can be administered by the customary methods, with oral or dermal administration being preferred, and/or administration by injection, such as intravenously, subcutaneously and/or intramuscularly. Oral administration is especially preferred.

One advantage of the invention-specific compounds is that they have improved ability to pass the blood-brain barrier. Due to this, the compounds are highly effective at their activity site, particularly in the brain cells. What is meant by "passing the blood-brain barrier" in the context of the invention is that the compounds can penetrate through the blood-brain barrier and into the brain, into the brain cells, especially into neurons. In especially advantageous embodiment forms, all or nearly all of the compounds reach the brain cells, and/or are fully or nearly fully available in the brain cells.

This is especially advantageous, since the amount of the compounds to be administered with the invention-specific compounds can be considerably smaller than with substances that manifest less ability to pass the blood-brain barrier. In advantageous fashion, side effects can be reduced by administering smaller doses.

Preferred dosages of the invention-specific compounds for administration to humans are in the area from $\geq 1$ mg per day per 75 kg of body weight to $\leq 1000$ mg per day per 75 kg of body weight, advantageously in the area from $\geq 10$ mg per day per 75 kg of body weight to $\leq 500$ mg per day per 75 kg of body weight, preferably in the area from $\geq 30$ mg per day per 75 kg of body weight to $\leq 100$ mg per day per 75 kg of body weight, and especially preferred in the area of >30 mg per day per 75 kg of body weight to <50 mg per day per 75 kg of body weight.

The invention-specific compounds are usable in advantageous embodiment forms, especially for therapeutic and/or prophylacic treatment, diagnosis and/or therapy for diseases that are connected with misfolding of proteins. Among these diseases, for example, are prion diseases and/or chronic degenerative diseases, especially neurodegenerative and/or neuropsychiatric diseases.

Under the term "misfolding of proteins," within the context of the invention, what is understood is that proteins may be misfolded or incorrectly processed.

In advantageous fashion, the invention-specific compounds can be used to treat plants and/or animals, tissues and/or cells. Especially the invention-specific compounds can be used to treat mammals such as humans.

The invention-specific compounds can have a positive influence on misfolding of proteins. Especially it was a surprise to find that preferred embodiment forms of the compounds can reduce the amount of misfolded prion proteins in cell culture models. In advantageous fashion, the invention-specific compounds reveal a higher effectiveness in influencing a misfolding of proteins than compounds known to date. Especially the invention-specific proteins can also demonstrate a greater effectiveness than combinations of substances known to date.

One particular advantage of the invention-specific compounds can be implemented in that the time from an infection to outbreak of the disease can be prolonged through administration of the invention-specific compounds, and/or the survival time after outbreak of the disease can be prolonged.

It is especially advantageous that the invention-specific compounds can lead to a reduction in misfolded proteins, especially prion proteins, even when the disease is advanced or clinical.

Experiments revealed that the invention-specific compounds (i.s.c.) reduce the cholesterol concentration on the cell surface. From this, applications also result for the i.s.c. to disturbances in the lipid-cholesterol metabolism. Additionally, an anti-parasitic—anti-protozoan effect is known from the acridines and phenothiazines. This effect is likewise attained by the i.s.c. and the result of this is applications to therapy of protozoa and parasitic diseases. We especially suspect that the invention-specific compounds may demonstrate a positive effect in treatment of trypanolysis.

Without being committed to a specific theory, we further suspect that the invention-specific compounds can have a positive effect in the treatment and/or prophylaxis of Alzheimer's disease, and especially can demonstrate a positive effect on prevention of Alzheimer's disease.

Correspondingly, a further subject of the invention relates to use of the invention-specific compounds, primarily of the overall formulas (10) to (14), to produce a medication for therapeutic and/or prophylactic treatment of diseases, selected from the group including:
  diseases that are connected with misfolding of proteins, like prion diseases and/or chronic degenerative diseases, especially neurodegenerative and/or neuropsychiatric diseases,
  diseases connected with increased cholesterol in the blood,
  diseases connected with a disturbance in the lipid metabolism, and/or hyperlipidemia,
  diseases connected with an inflammation, like chronic inflammations, cardiovascular diseases, especially arteriosclerosis, and/or infections in animals and plants evoked by parasites, especially in humans and commercially useful animals, diseases caused by protozoa and/or worms, especially cerebral infections caused by parasites and/or protozoa.

The prion diseases can especially be selected from the group including Creutzfeld-Jakob Disease, Gerstmann-Sträussler-Scheinker Disease, Fatal Familial Insomnia (FFI), kudu, scrapie and/or bovine spongiform encephalopathy (BSE).

Chronic degenerative diseases, particularly neurodegenerative and/or neuropsychiatric diseases, have preferably been selected from the group including Alzheimer's, amyotrophic lateral sclerosis (ALS), Pick's Disease, Parkinson's, multiple sclerosis, Huntington's chorea, type I and type II diabetes, autism, schizophrenia, bipolar diseases, depression, polyglutamine diseases, fronto-temporal dementia, tauopathies, multiple system atrophy, sleep disturbances, plasma cell dyscrasia, familial amyloid polyneuropathy, medullar thyroid carcinomas, chronic renal insufficiency, congestive heart failure, amyloidoses like cardiac amyloidosis, systemic amyloidosis and/or familial amyloidosis.

Preferred neurodegenerative and/or neuropsychiatric diseases are selected from the group including Alzheimer's, fronto-temporal dementia, Parkinson's, tauopathies, multiple system atrophy, amotrophic lateral sclerosis (ALS), schizophrenia, bipolar diseases, depression, polyglutamine diseases, multiple sclerosis and/or sleep disturbances.

Especially in treatment of neurodegenerative diseases in humans an advantageous effect can be attained on the course of the illness by use of the invention-specific compounds, and in particular the appearance of misfolded proteins can be reduced. A further advantage of the invention-specific compounds can result from the fact that they can be used in low doses. Additionally, the result of this is that no side effects, or only slight ones, appear. This makes it possible to administer the invention-specific compounds over a longer period of time. This, for example, makes possible administration for treatment of neurodegenerative diseases, therapy for which must under certain circumstances continue for months or years.

In especially advantageous embodiment forms, the invention-specific compounds can lead to a lowering of blood cholesterol. This, for example, makes possible, an application for disturbances in lipid metabolism or hyperlipidemia. Additionally, the compounds can manifest anti-inflammatory effects and be used for therapeutic and/or prophylactic treatment of cardiovascular diseases, especially for prophylaxis of arteriosclerosis.

Additionally, the compounds are usable in advantageous fashion also for therapeutic and/or prophylactic treatment of malaria and other parasite-caused infections in living creatures, animals and plants, especially commercially useful animals and humans, such as malaria, trypanosomiasis, sleeping sickness, amoebiasis, leishmaniosis and/or toxoplasmosis. Also, application as an anti-protozoan agent and/or as an anti-helminthic, for example, against nematodes like pinworms (enterobius), ascaris, ascaris in dogs and cats (toxocara), whipworm (trichuris), hookworm (nacator, anchylostoma), strongyloid threadworm (spobngyloides), guinea worm (dracunculus), or filarial, zestodes, and/or trematodes.

One great advantage in using the invention-specific compounds, preferably of the formula (10) can be implemented in that they possess better ability to pass the blood-brain barrier, and can demonstrate better effectiveness with cerebral parasites and/or protozoan infections like cerebral malaria, toxoplasmosis and/or cerebral abcesses.

Without being bound to a specific theory, we further suspect that the invention-specific compounds, preferably of formula (10), can demonstrate an inhibiting effect on so-called multi-drug resistance (MDR) proteins, like the P-glycoprotein, so that better effectiveness and bioavailability can be offered in comparison to known substances.

In advantageous fashion, the invention-specific compounds exhibit slight, or negligible, toxicity when administered. This, for example, makes possible administration in high doses, especially one-time and/or multiple, temporally limited administration in dosages in the area of $\geq 10$ mg per day per 75 kg of body weight up to $\leq 1000$ mg per day per 75 kg of body weight, for example over a time period of at least three months. The slight or negligible toxicity of the invention-specific compounds also makes possible administration in so-called pulsed therapy. With this, doses in the area of $\geq 10$ mg per day per 75 kg of body weight up to $\leq 1000$ mg per day per 75 kg of body weight can, for example, be administered for one week, preferably at least twice for a week, interrupted by a period with no administration. Such an administration can further improve the positive effect of the compounds on misfolded proteins.

A further subject of the invention relates to medications including invention-specific compounds, preferably including compounds of formulas (10) to (14).

Medications including invention-specific compounds are applicable for treatment in vivo and in vitro. One preferred use of the medications including invention-specific compounds is therapeutic and/or prophylactic treatment of diseases connected with misfolding of proteins, like prion diseases and/or chronic degemerative diseases, especially neurodegenerative and/or neuropsychiatric diseases.

A further subject of the invention relates to anti-prion agents, including invention-specific compounds, preferably compounds of the formula (10).

The term "anti-prion agents" in the context of this invention has the meaning that the agent including invention-specific compounds can positively influence prion diseases. Especially, the quantity of misfolded prion proteins ($PrP^{Sc}$) can be reduced.

In preferred embodiment forms, use of the invention-specific compounds can result in a dropoff in the quantity of misfolded proteins, especially prion proteins ($PrP^{Sc}$), in the investigated media, cells, tissues and/or organs, and/or the appearance of misfolded proteins can be totally or almost totally avoided.

For example, in experiments, the invention-specific compounds reveal themselves to be more active as compared with known substances or combinations of them. Thus, the invention-specific compounds can cause the quantity of misfolded prion proteins to decline to a greater extent than with administration of individual known substances or combinations of them.

A further subject relates to the use of invention-specific compounds, preferably of compounds of the overall formula (10), for purification of biological fluids, especially body fluids, that contain misfolded proteins, preferably prions, especially from cell suspensions. The invention-specific compounds can especially be used for purification of biological fluids contaminated with misfolded proteins, preferably prions.

The term "purification" in the context of this invention has the meaning that in biological fluids, the quantity of misfolded proteins is reduced after a dosage of the invention-specific compounds, and especially the term "purification" in the context of this invention can be understood in the meaning of the terms "clearing" or "clearance." Especially, the invention-specific compounds, in particularly advantageous embodiment forms, can lead to a complete or almost complete elimination of the misfolded proteins.

The cell suspensions can, for example, be cerebrospinal fluid, preferably the cell suspensions are selected from the group including blood and/or or blood products.

For this, the fluids can be removed from the organism and the invention-specific compounds can be added outside the organism, or the invention-specific compounds can be added to the fluids without these being removed from the organism.

Yet another subject of the invention relates to procedures for purification of biological fluids that contain misfolded proteins, preferably prions, whereby invention-specific compounds, preferably of the formulas (10) to (14) are added to the biological fluid to be purified, especially cell suspensions like blood or blood products. Optionally, the compounds can again be separated from the biological fluid to be purified by, for example, chromatography, dialysis and/or adsorption, after an incubation.

In further advantageous embodiment forms of the procedure, the biological fluid, before and after the dosing of invention-specific compounds, can be tested using suitable methods for the quantity of misfolded proteins contained.

In advantageous embodiment forms of the procedure, the biological fluid to be purified, especially cell suspensions like blood or blood products, can first be removed from the organism, for example by punction, and after purification be returned to the organism, for example by phasmapheresis.

In especially advantageous embodiment forms of the procedure for purification of biological fluids like cell suspensions, especially blood, this includes the following steps:
a) optional removal of the biological fluid from an organism, for example by puncture;
b) incubation of the biological fluid with the invention-specific compounds;
c) optional separation of the compounds, for example by chromatography, dialysis and/or adsorption;
d) optional re-insertion of the biological fluid, for example by plasmapheresis.

Alternatively, for example, the fluids can be stored in the form of stored blood and/or placed back at a later time into the organism from which they were removed.

Examples and figures that serve to illustrate the present invention, are given in what follows.

Shown in the figures are:

FIG. 1 Western blots of cell lysates of ScNa2 cells digested by Protease K, that show the bands of misfolded prion proteins. Here Sc stands for the negative check of untreated cells, that shows clear bands of the misfolded prion protein, Q stands for cells treated as positive controls with 1 μm of Quinacrin, which reveal no bands of the misfolded prion protein.

It can be recognized that in cell cultures that were incubated with a concentration of 0.1 μM and 0.3 μM of the compound of formula (10), in the lysates no misfolded prion proteins could be documented, while the cells treated with the identical concentration of Quinacrin still contained misfolded prion proteins.

EXAMPLE 1

Manufacture of 6-chlor-2-methoxy-acridine-9-yl)-(4-{4-[3-(10,11-dihydro-dibenzo[b,f]azepine-5-yl)-propyl]-piperazine-1-yl}-butyl)-amine Na(Oac)$_3$BH$_3$ (171 mg, 0.80 mmol) were added to a solution of 3-(10,11-dihydro-dibenzo[b,f]azepine-5-yl)-propionaldehyde (100 mg, 0.40 mmol) and N-(3-cyanopropyl)-piperazine (122 mg, 0.80 mmol) in CH$_2$Cl$_2$ (10 ml). After 16 hours of stirring, the mixture was diluted with CH$_2$Cl$_2$ (50 ml) and washed with a saturated solution of NaHCO$_3$. The organic phase was dried (Na$_2$SO$_4$) and evaporated. Purification using flash chromatography of the residue obtained yielded N-[3-(10,11-dihydro-dibenzo[b,f]azepine-5-yl)-propyl]-N'-(3-cyanopropyl)-piperazine (yield: 106 mg, 68%).

N-[3-(10,11-dihydro-dibenzo[b,f]azepine-5-yl)-propyl]-N'-(3-cyanopropyl)-piperazine (60 mg, 0.15 mmol) was dissolved in dried diethylether (Et$_2$O) (5 ml) and mixed with LiAlH$_4$ (1.0 M in Et$_2$O, 0.15 ml, 0.15 mmol) at 0° C. After a reaction time of 3 hours, 3 drops of 0.5 N NaOH were added and the mixture was filtered via silica gel (Celite®, 521 AW) and MgSO$_4$. Evaporation of the solvent yielded 48 mg N-[3-(10,11-dihydro-dibenzo[b,f]azepine-5-yl)-propyl]-N'-(3-aminopropyl)-piperazine, which was dissolved during mild heating in 1.5 g of phenol. Addition of 6,0-dichloro-2-methoxy-acridine (70 mg, 0.25 mmol) was followed by 1 hour of stirring at 100° C. Subsequent addition of aqueous NaOH, extraction with EtOAc and vaporization of the organic phase yielded 6-chlor-2-methoxy-acridine-9-yl)-(4-{4-[3-(10,11-dihydro-dibenzo[b,f]azepine-5-yl)-propyl]-piperazine-1-yl}-butyl)-amine, which was purified via flash chromatography, in a yield of 21%.

EXAMPLE 2

Isolation and Purification of a Polyclonal Chicken Anti-Mouse Prion Protein Antibody Immunoglobin Isolation:

Eggs from chickens immunized with recombinant mouse prion proteins (recMoPrP) were collected. The egg yolks were diluted at a 1:5 ratio in cold 20 mM sodium acetate solution, pH 5.2, and kept overnight at 4° C. After centrifuging to remove insoluble material at 20,000×g for 20 minutes, the immunoglobin was precipitated by addition of 20% (w/v) of (NH$_4$)SO$_4$ and centrifuged after 2 hours at 4° C. at 20,000×g for 20 minutes. The palletized immunoglobin was dissolved in a solution of 20 mM Tris pH 8, 150 mM NaCl, 0.1% tween-20, 1 mM EDTA.

Purification:

Recombinant mouse prion protein (recMoPrP) was dissolved in a suspension of NHS-activated sepharose from Amersham Pharmacia, pre-washed according to the directives of the manufacturer's protocol, in a cold (4° C.) solution of 50 mM of NaHCO$_3$, pH 8.3, 1% triton X-100, 20% DMSO at 3 mg of protein per ml of resin. This suspension was stirred overnight at 4° C. Free NHS groups were then blocked with 50 mM glycine for 1 hour at room temperature. The resin was then washed consecutively with solutions of 50 mM Tris ph 9, 50 mM glycine pH 3, and finally 20 mM Tris pH 8, 150 NaCl, 0.2% triton X100, 0.2% Tween-20, 2 mH EDTA. In this buffer, immobilized recombinant mouse prion protein (recMoPrP) was mixed with anti-mouse prion protein immunoglobin (approximately 200 mg of immunoglobin per mg of mouse prion protein) and stirred overnight at 4° C. The resin was then collected and thoroughly washed, and then elutriated with a solution of 100 mM glycine pH 3, 1 M NaCl, 1% triton X-100, whereby the pH was then immediately set to 8.

The purified anti-mouse prion protein immunoglobin was then tagged with EZ-Link™ maleimide activated horseradish peroxidase (HRP) from Pierce Chemical, Rockford, Ill., according to the directives of the manufacturer's protocol.

This antibody merely recognizes the non- and monoglycosiliated form of the prion protein, that corresponds to the misfolded prion protein, but not the diglycosliated form.

EXAMPLE 3

Cell Culture Trials with Compounds of Formulas (12), (13) and (14)

Mouse neuroblastoma cells (N2a) were infected with mouse-adapted scrapie prions and subcloned (Bosque, P. J. and S. B. Prusiner (2000) "Cultured cell sublines highly susceptible to prion infection"—J Virol 74(9): 4377-86) and cultivated. Confluent 10-cm cell culture dishes were split, a drop with $2\text{-}5*10^4$ of the mouse neuroblastoma cells (ScN2a) infected with mouse-adapted scrapie prions was added into a 60-mm cell culture dish and cultivated with 4 ml MEM from Invitrogen of Carlsbad, U.S.A., containing 10% (vol/vol) of fetal calf serum (FCS), penicillin-streptomycin (100 units per ml) and L-glutamine (2 mM) for one week with 0.1 µM, 0.5 µM and 1 µM of compound (12) and (14) and 0.1 µM and 0.5 µM of compound (13). During the week, on every $2^{nd}$ day, the medium was changed and the appropriate quantity of the tested compound was added to the medium.

After 7 days the cells were washed once with PBS (137 mM NaCl, 2.7 mM KCl, 10 mM $Na_2HPO_4$ 2 mM $KH_2PO_4$) and lysated in a lysis buffer (10 mM Tris, ph 8.0, 150 mM NaCl, 0.5% triton X-100, 0.5% deoxycholate). The lysates were then digested with Proteinase K from Merck in Darmstadt (20 µg per ml, 30 minutes, 37° C.) and the reaction was stopped with 2 mM of PMSF (phenylmethylsulfionyl fluoride). Then the digested lysates were centrifuged for 45 minutes at 4° C., 100,000 g, the excess was removed, and the pellets were absorbed into yellow charging buffer (100 mM Tris-Cl pH 6.8, 4% (w/v) SDS, 0.2% (w/v) bromphenol blue, 20% (v/v) glycerol, 200 mM β-mercaptoethanol). The samples are separated via an SDS gel (4-20%, Biorad) and the prion protein is detected with 0.3 µg per ml of the antibody according to example 2 by western blotting (Enhanced Chemiluminescence (ECL) System from Amersham Pharmacia).

Mouse neuroblastoma cells infected with mouse-adapted scrapie prions served as negative controls, which were not treated with Quinacrin. Cells that were treated with the known anti-prion substance Quinacrin under trial conditions with 1 µm served as the positive controls.

The misfolded form of the prion protein was not destroyed due to treatment with Proteinase K and was detectable in the western blot.

It was shown that the compounds (12), (13) and (14) demonstrated an elimination of the misfolded prion protein in the infected cells, with compounds (12) and (13) having greater effectiveness than compound (14).

EXAMPLE 4

In correspondence to the conditions of example 3, mouse neuroblastoma cells infected with mouse-adapted scrapie prions were incubated with 0.05 µM, 0.075 µM, 0.1 µM and 0.3 µM of the compound of formula (10), and processed, and the misfolded prion proteins were detected in western blot.

Mouse neuroblastoma cells infected with mouse-adapted scrapie prions served as negative controls, which were not treated with Quinacrin. Cells that were treated with the known anti-prion substance Quinacrin under trial conditions with 1 µm served as the positive controls. As comparisons, cells that were treated with 0.1 µM and 0.3 µM of Quinacrin were treated.

It was shown that in cell cultures that were incubated with a concentration of 0.1 µM and 0.3 µM of the compound of formula (10), in the lysates, no misfolded prion proteins could be detected, while the cells treated with the identical concentration of Quinacrin still contained misfolded prion proteins. Compound (10) revealed itself to be about 10 times more active than Quinacrin.

The western blot depicted in FIG. 1 makes clear the trial results of example 4.

EXAMPLE 5

Filipin Staining

The cells were applied onto cover slips and treated as in examples 3 and 4 with 0.25 µM of compound (10) and 1 µM of Quinacrin. On the sixth day of the treatment, the cells were washed once with ice-cold PBS (137 mM NaCl, 2.7 mM KCl, 10 mM $Na_2HPO_4$, 2 mM $KH_2PO_4$). Then the cells were fixed with 4% (w/v) of paraformaldehyde in PBS for 30 minutes at room temperature. Then the paraformaldehyde solution was removed and the cells were incubated with filipin (50 µg per ml in PBS from Sigma) for 30 minutes at room temperature. The cover slips were washed 4 times with PBS and investigated under the microscope with the appropriate filter sets. The filipin staining detects cellular cholesterol.

It was shown that with the untreated cells (ScN2a), the cholesterol is predominantly to be found on the cell surface. In the cells treated with compound (10), a redistribution was revealed to intracellular compartments, just as in the cells treated with Quinacrin. This shows the effect of the compounds on cholesterol.

EXAMPLE 6

Activity Trials In Vivo on a Mouse Model

The effect of the compound according to formula (10) on a prion infection in vivo was investigated in a mouse model of the prion disease.

Transgene mice (TG 20, Fischer et al., 1996, EMBO Journal, vol. 15, pp. 1255-64) were used, which additionally superexpressed the endogenous mouse protein PrP to endogenous mouse PrP-Gen. These mice have a shortened incubation time for prions of 92±4 days, because, due to the high concentration of prion proteins ($PrP^C$) in the brain, prions multiply especially quickly, so that acting against this accelerated conversion is necessary.

These mice were inoculated three weeks before the start of the trials intracerebrally with 100 µl of a $10^{-5}$ diluted RML scrapie-containing cerebral homogenate (Chandler, Lancet, 1961, vol. 1, pp. 1378-79). Thus at the start of the trials already a positive effect was made difficult, because neurotoxic effects and/or subclinical brain damage could arise.

The compound according to the formula (10) was first dissolved in ethanol, and then, in Distel oil, diluted in an ending concentration of 10 mg per ml. Then the compound was applied via a stomach probe, in Gavage feeding mode, to a group of 11 mice, three times weekly on Monday, Wednesday and Friday, for eight weeks, at a dose of 2 mg per 200 µl per mouse.

A control group of mice that were not treated with the compound according to formula (10), correspondingly died after 92±4 days of prion disease, while the mice that were treated with the compound according to formula (10), died only after 100±5 days.

Thus, we found a lengthening of the survival time by 10%, determined using Student's t test (p<0.0001), under the trial conditions. These conditions come close to the clinical situation in which patients with Creutzfeldt-Jakob disease only seek medical help in the later stages.

The invention claimed is:
1. A compound according to formula (1):

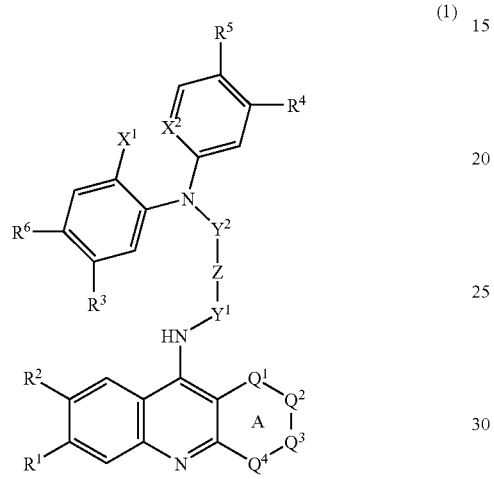

(1)

wherein:
A is a six-link, unsaturated or saturated ring;
$Q^1, Q^2, Q^3, Q^4$ are each selected, independent of each other, from the group consisting of CH, C-halogen, C—O—($C_1$-$C_{10}$)-alkyl, C—$CF_3$, C—CN and $CH_2$;
$R^1, R^2, R^3, R^4, R^5, R^6$, are each selected, independent of each other, from the group consisting of H, Halogen, $C_1$-$C_{10}$-alkyl, $C_1$-$C_{10}$-alkenyl, $C_1$-$C_{10}$-alkynyl, $C_1$-$C_{10}$-alkyloxy, $CF_3$, $NH_2$, and $NHR^9$, whereby the radical $R^9$, is selected from the group consisting of $C_1$-$C_{10}$-alkyl, $C_1$-$C_{10}$-acyl, $NO_2$, and CN;
$X^1$ and $X^2$ each are H, or $X^1$ and $X^2$ jointly form X, whereby:
X is selected from the group consisting of $CH_2$, $CH_2$—$CH_2$, CH=CH, O and S;
$Y^1, Y^2$ each, independent from each other, are unbranched or branched $C_1$-$C_{10}$-alkyl;
Z is a structure element Z1 or Z2 as given below, whereby:
Z1 has the following general formula (2):

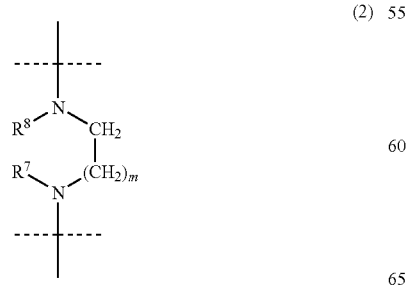

(2)

wherein:
m is 1, 2, 3, 4, 5 or 6,
$R^7, R^8$, are selected independently of each other from the group consisting of H, $C_1$-$C_{10}$-alkyl and $C_1$-$C_{10}$-acyl, or $R^7$ and $R^8$ are each $CH_2$ and can form a ring via a $CH_2$—$CH_2$ bond; and
Z2 has the following general formula (3):

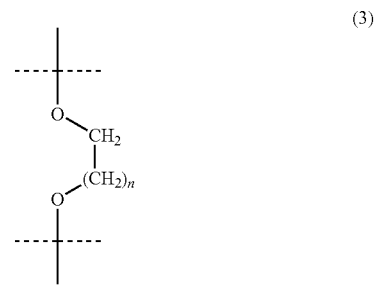

(3)

wherein:
n is 2, 3, 4, 5 or 6.
2. The compound according to claim 1, wherein Z1 has the formula (7):

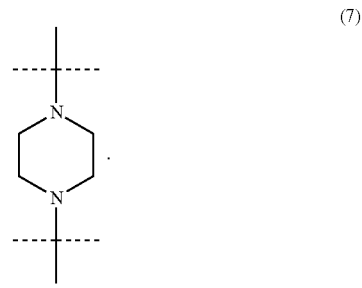

(7)

3. The compound according to claim 1, wherein the compound has the formula (9):

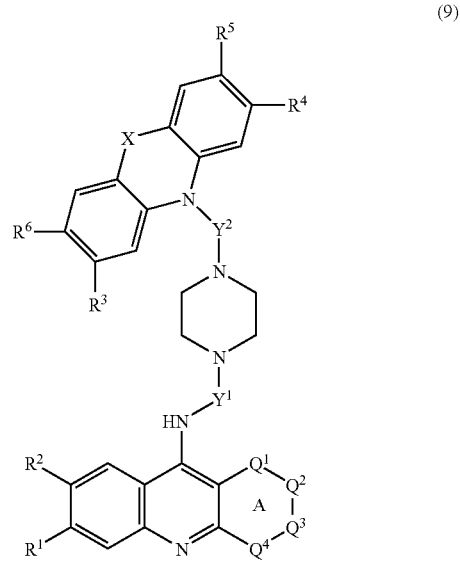

(9)

wherein:

A is a six-link, unsaturated or saturated ring;

$Q^1, Q^2, Q^3, Q^4$ are each selected, independent of each other, from the group consisting of CH, C-halogen, C—O—($C_1$-$C_{10}$)-alkyl, C—$CF_3$, C—CN and $CH_2$;

$R^1, R^2, R^3, R^4, R^5, R^6$, are each selected, independent of each other, from the group consisting of H, Halogen, $C_1$-$C_{10}$-alkyl, $C_1$-$C_{10}$-alkenyl, $C_1$-$C_{10}$-alkynyl, $C_1$-$C_{10}$-alkyloxy, $CF_3$, $NH_2$, and $NHR^9$, whereby the radical $R^9$, is selected from the group consisting of $C_1$-$C_{10}$-alkyl, $C_1$-$C_{10}$-acyl, $NO_2$, and CN;

X is selected from the group consisting of $CH_2$, $CH_2$—$CH_2$, CH=CH, O and S; and $Y^1, Y^2$ each, independent from each other, are unbranched or branched $C_1$-$C_{10}$-alkyl.

4. The compound according to claim 1, wherein:

$Q^1, Q^3$, and $Q^4$ each are CH; and $Q^2$ is selected from the group consisting of CH and C—O—$CH_3$.

5. The compound according to claim 1, wherein:

$Q^1, Q^2, Q^3$, and $Q^4$ each are $CH_2$.

6. The compound according to claim 1, wherein:

$Y^1$ and $Y^2$ independent of each other, are each selected from the group consisting of —$(CH_2)_o$— and —CH($CH_3$)—$(CH_2)_p$—, whereby:

o is 2, 3, 4, 5 or 6; and p is 2, 3, 4 or 5.

7. The compound according to claim 1, wherein:

$R^1, R^2, R^3, R^4, R^5$, and $R^6$ are each selected, independent of each other, from the group consisting of H, halogen, $NH_2$, and $NHR^9$, whereby the radical $R^9$ is selected from the group consisting of $C_1$-$C_5$-alkyl, $C_1$-$C_5$-acyl, $NO_2$, and $C_1$-$C_5$-alkyloxy.

8. The compound according to claim 1, wherein:

X is S or —$CH_2$—$CH_2$—.

9. The compound according to claim 4, wherein:

$Y^1, Y^2$ independent of each other, are each selected from the group consisting of —$(CH_2)_o$— and —CH($CH_3$)—$(CH_2)_p$—, whereby:

o is 2, 3, 4, 5 or 6; and p is 2, 3, 4 or 5.

10. The compound according to claim 4, wherein:

$Y^1, Y^2$ independent of each other, are —$(CH_2)_o$—, whereby:

o is 3, 4 or 5.

11. The compound according to claim 10, wherein:

$R^1, R^2, R^3, R^4, R^5$, and $R^6$ are each selected, independent of each other, from the group consisting of H and Cl.

12. The compound according to claim 1, wherein the compound has the formula (10):

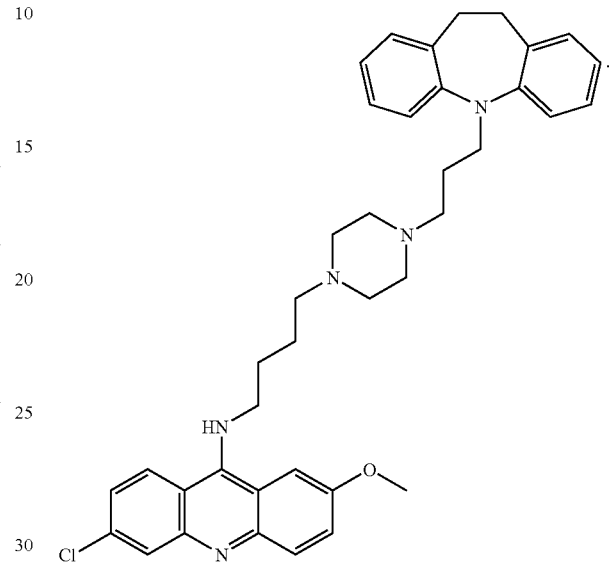

(10)

13. The compound according to claim 1, wherein the compound has the formula (12):

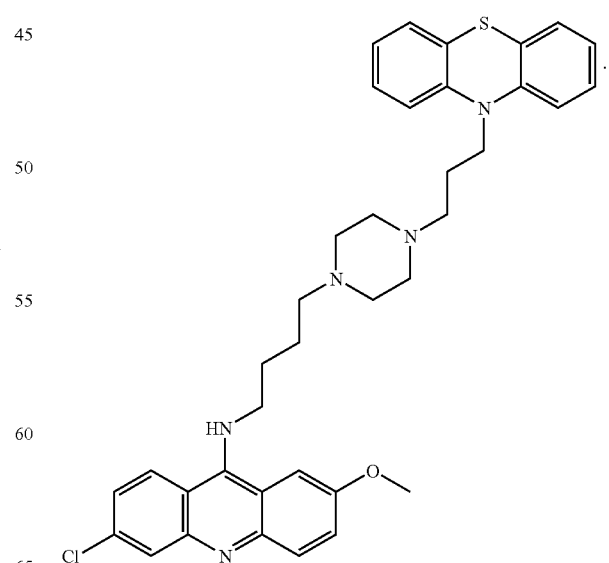

(12)

14. The compound according to claim 1, wherein the compound has the formula (13):

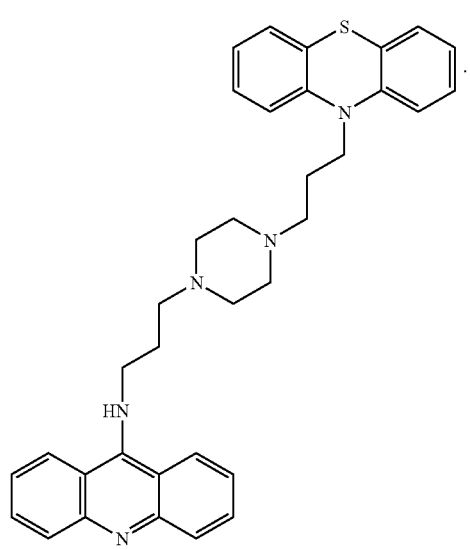

(13)

15. The compound according to claim 1, wherein the compound has the formula (14):

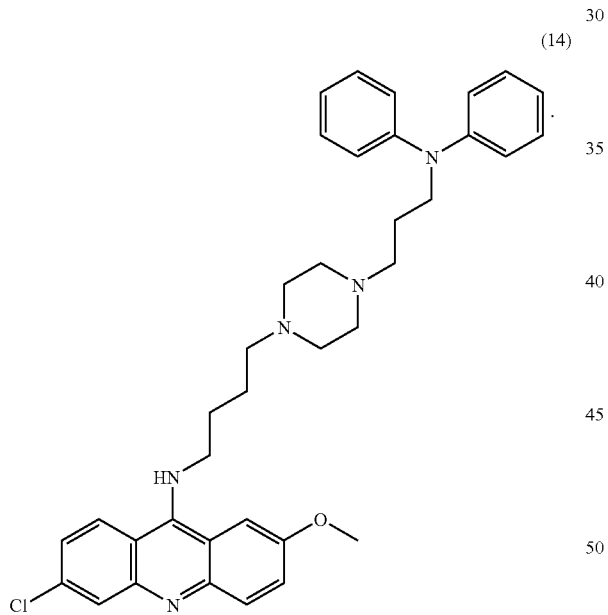

(14)

16. A medication comprising the compound according to claim 1.

17. The compound according to claim 7, wherein the halogen is selected from the group consisting of F, Cl and Br.

18. The compound according to claim 7, wherein the $C_1$-$C_5$-alkyl is selected from the group consisting of methyl, ethyl, isopropyl and tert-butyl.

19. The compound according to claim 7, wherein the $C_1$-$C_5$-alkyloxy is selected from the group consisting of —O-methyl, —O-ethyl, —O-isopropyl and —O-tert-butyl.

20. An enantiomer, diastereomer or a pharmaceutically compatible salt of the compound according to claim 1.

21. An enantiomer, diastereomer or a pharmaceutically compatible salt of the compound according to claim 3.

22. An enantiomer, diastereomer or a pharmaceutically compatible salt of the compound according to claim 12.

23. An enantiomer, diastereomer or a pharmaceutically compatible salt of the compound according to claim 13.

24. An enantiomer, diastereomer or a pharmaceutically compatible salt of the compound according to claim 14.

25. An enantiomer, diastereomer or a pharmaceutically compatible salt of the compound according to claim 15.

* * * * *